United States Patent [19]

Glock et al.

[11] Patent Number: 5,371,060
[45] Date of Patent: Dec. 6, 1994

[54] SELECTIVE HERBICIDAL COMPOSITION COMPRISING 1,5-DIPHENYLPYRAZOLE-3-CARBOXYLIC ACID SAFENERS AND SULFONYLUREA HERBICIDES

[75] Inventors: Jutta Glock, Kaisten, Switzerland; Elmar Kerber, Görwihl, Germany

[73] Assignee: Ciba-Geigy Corporation, Ardsley, N.Y.

[21] Appl. No.: 19,947

[22] Filed: Feb. 19, 1993

[30] Foreign Application Priority Data

Feb. 26, 1992 [CH] Switzerland ............................ 583/92
Aug. 31, 1992 [CH] Switzerland .......................... 2727/92

[51] Int. Cl.$^5$ ............................................ A01N 25/32
[52] U.S. Cl. .................................................. 504/106
[58] Field of Search ................... 504/106; A01N 25/32

[56] References Cited

U.S. PATENT DOCUMENTS

| | | | |
|---|---|---|---|
| 4,419,121 | 12/1983 | Meyer et al. | 71/92 |
| 4,544,401 | 10/1985 | Levitt | 71/92 |
| 4,579,583 | 4/1986 | Föry et al. | 71/92 |
| 4,618,363 | 10/1986 | Gass et al. | 504/213 |
| 4,634,465 | 1/1987 | Ehrenfreund et al. | 71/91 |
| 4,643,760 | 2/1987 | Meyer et al. | 71/92 |
| 4,671,819 | 6/1987 | Meyer et al. | 71/93 |
| 4,780,125 | 10/1988 | Meyer et al. | 71/93 |
| 4,944,790 | 7/1990 | Moser et al. | 504/106 |
| 4,946,494 | 8/1990 | Taylor | 71/91 |
| 5,078,780 | 1/1992 | Moser et al. | 71/92 |
| 5,114,462 | 5/1992 | Moser et al. | 71/88 |

FOREIGN PATENT DOCUMENTS

| | | |
|---|---|---|
| 1240531 | 8/1988 | Canada . |
| 1243675 | 10/1988 | Canada . |
| 0459949 | 4/1991 | European Pat. Off. . |
| 0492367 | 7/1992 | European Pat. Off. . |

OTHER PUBLICATIONS

Derwent Abstract of EP 492,367 1990.
*The Agrochemicals Handbook* "Diclofay-methyl" Aug. 1987.

Ashton, F. M. et al. *Mode of Action of Herbicides* pp. 396–397. 1981.

*Primary Examiner*—Richard L. Raymond
*Assistant Examiner*—S. Mark Clardy
*Attorney, Agent, or Firm*—Marla J. Mathias; Edward McC. Roberts

[57] ABSTRACT

A selective herbicidal composition for controlling grasses and weeds in crops of useful plants is composed of a) a herbicidally effective amount of a sulfonylurea of the formula I

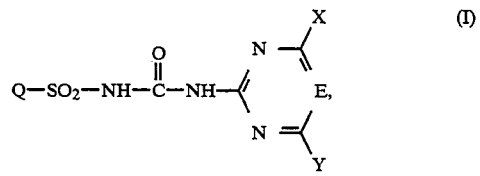

in which

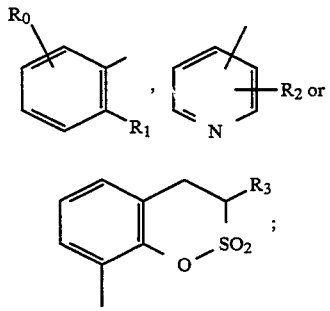

$R_0$ is hydrogen, halogen, methyl or methoxy; $R_1$ is halogen, $C_1$–$C_3$haloalkyl, $C_1$–$C_3$haloalkoxy, $C_1$- or $C_2$alkoxy-$C_1$–$C_3$alkoxy, $C_3$–$C_6$alkenyloxy, $C_3$–$C_6$alkynyloxy, $C_2$- or $C_3$alkynyl, (Abstract continued on next page.)

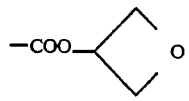

or a radical

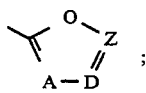

A and Z independently of one another are nitrogen or methine; D is nitrogen, methine or methylmethine; $R_2$ is $C_1$–$C_3$haloalkoxy, $C_1$- or $C_2$alkoxy-$C_1$–$C_3$alkoxy, $C_4$–$C_6$cycloalkyloxy, $C_3$–$C_6$cycloalkyl-$C_1$–$C_3$alkoxy, —COOR$_4$ or —NR$_5$R$_6$; $R_4$ is $C_1$–$C_3$alkyl or 3-oxetanyl; $R_5$ is hydrogen or $C_1$–$C_4$alkyl; $R_6$ is hydrogen, $C_1$–$C_4$alkyl or —COR$_{11}$; $R_{11}$ is hydrogen or $C_1$–$C_6$alkyl; $R_3$ is hydrogen or methyl; X is halogen, methyl, ethyl, methoxy, ethoxy, $C_1$- or $C_2$haloalkoxy, cyclopropyl, —NHCH$_3$ or —N(CH$_3$)$_2$; Y is methyl, ethyl, methoxy, ethoxy, $C_1$- or $C_2$-haloalkoxy or cyclopropyl; and E is nitrogen or the methine group; and the agrochemically acceptable salts of these compounds, in which D and Z must not simultaneously be nitrogen; and E is the methine group if X is halogen or difluoromethoxy; and b), as safener, a herbicide-antagonistically effective amount of a 1,5-diphenylpyrazole-3-carboxylic acid derivative of the formula II

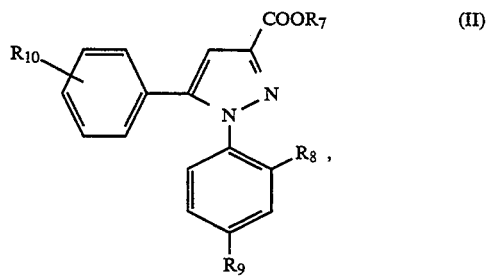

in which $R_7$ is hydrogen, $C_1$–$C_8$alkyl, $C_3$–$C_6$alkenyl, $C_3$–$C_6$cycloalkyl-$C_1$–$C_3$alkyl, or an alkali metal or ammonium cation; and $R_8$, $R_9$ and $R_{10}$ independently of one another are hydrogen or halogen.

16 Claims, No Drawings

SELECTIVE HERBICIDAL COMPOSITION COMPRISING 1,5-DIPHENYLPYRAZOLE-3-CARBOXYLIC ACID SAFENERS AND SULFONYLUREA HERBICIDES

The present invention relates to a selective herbicidal composition for controlling grasses and weeds in crops of useful plants, in particular in cereal crops, which comprises a herbicide and a safener (antagonist, antidote) protecting the useful plants but not the weeds against the phytotoxic action of the herbicide, and to the use of this composition, or of the combination of herbicide and safener (antagonist, antidote) for controlling weeds in crops of useful plants.

When herbicides are applied, the crop plants can be damaged to a considerable extent depending on factors such as, for example, dosage rate of the herbicide and how it is applied, crop plant species, constitution of the soil and climatic conditions, for example day length, temperature and amount of precipitation. Severe damage may result in particular when, in connection with crop rotation, crop plants which are resistant to herbicides are followed by other crop plants which have no, or only insufficient, resistance to the herbicides.

To solve this problem, a variety of substances have been proposed which are capable of specifically antagonising the damaging effect of the herbicide on the crop plant, i.e. of protecting the crop plant without noticeably affecting the herbicidal activity on the weeds to be controlled. It has emerged that the safeners proposed frequently act in a highly species-specific manner, both with regard to the crop plants and with regard to the herbicide, and if appropriate also as a function of how the safener is applied, which means that a certain safener is frequently only suitable for a particular crop and one class of herbicidal substances. For example, EP-A-0 268 554 discloses 1,5-diphenylpyrazole-3-carboxylic acid derivatives which protect crop plants against the phytotoxic action of phenoxypropionic ester herbicides.

It has now been found that these 1,5-diphenylpyrazole-3-carboxylic acid derivatives are suitable for protecting crop plants against the phytotoxic action of a specific class of sulfonylurea herbicides.

There is therefore proposed according to the invention a selective herbicidal composition which comprises, besides inert ingredients such as carriers, solvents and wetting agents, as effective component a mixture composed of a) a herbicidally effective amount of a sulfonylurea of the formula I

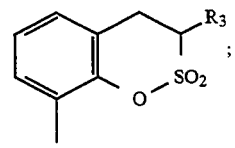

in which Q is a radical

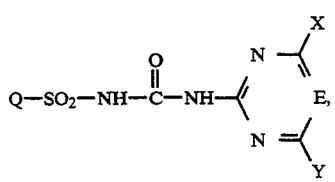,
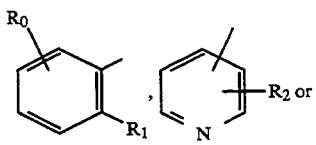

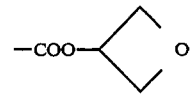

$R_0$ is hydrogen, halogen, methyl or methoxy; $R_1$ is halogen, $C_1$-$C_3$haloalkyl, $C_1$-$C_3$haloalkoxy, $C_1$- or $C_2$alkoxy-$C_1$-$C_3$alkoxy, $C_3$-$C_6$alkenyloxy, $C_3$-$C_6$alkynyloxy, $C_2$- or $C_3$alkynyl,

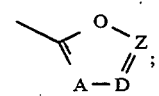

or a radical $$\begin{array}{c} \diagup O_{\diagdown Z} \\ \diagup\!\!\!\diagdown \!\!\!\diagup\!\!\!\diagdown \\ A-D \end{array};$$

A and Z independently of one another are nitrogen or methine; D is nitrogen, methine or methylmethine; $R_2$ is $C_1C_3$haloalkoxy, $C_1$- or $C_2$alkoxy-$C_1$-$C_3$alkoxy, $C_4$-$C_6$-cycloalkyloxy, $C_3$-$C_6$cycloalkyl-$C_1$-$C_3$alkoxy, —COOR$_4$ or -NR$_5$R$_6$; R$_4$ is $C_1$-$C_3$alkyl or 3-oxetanyl; R$_5$ is hydrogen or $C_1$-$C_4$alkyl; R$_6$ is hydrogen, $C_1$-$C_4$alkyl or —COR$_{11}$; R$_{11}$ is hydrogen or $C_1$-$C_6$alkyl; R$_3$ is hydrogen or methyl; X is halogen, methyl, ethyl, methoxy, ethoxy, $C_1$-or $C_2$haloalkoxy, cyclopropyl, —NHCH$_3$ or —N(CH$_3$)$_2$; Y is methyl, ethyl, methoxy, ethoxy, $C_1$- or $C_2$-haloalkoxy or cyclopropyl; and E is nitrogen or the methine group; and the agrochemically acceptable salts of these compounds, in which D and Z must not simultaneously be nitrogen; and E is the methine group if X is halogen or difluoromethoxy; and b), as safener, a herbicide-antagonistically effective amount of a 1,5-diphenylpyrazole-3-carboxylic acid derivative of the formula II

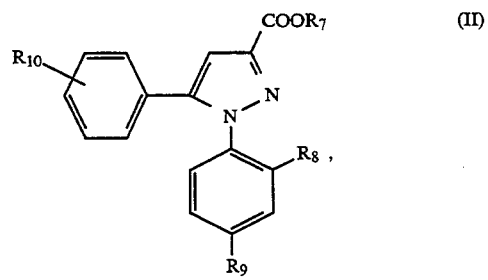

in which R$_7$ is hydrogen, $C_1$-$C_8$alkyl, $C_3$-$C_6$alkenyl, $C_3$-$C_6$cycloalkyl-$C_1$-$C_3$alkyl, or an alkali metal or ammonium cation; and R$_8$, R$_9$ and R$_{10}$ independently of one another are hydrogen or halogen.

In the compounds of the formulae I and II, halogen is fluorine, chlorine, bromine or iodine; preferably fluorine, chlorine or bromine, in particular fluorine and chlorine.

Suitable as alkyl groups are straight-chain or branched alkyl groups, for example methyl, ethyl, n-propyl, iso-propyl, n-butyl, iso-butyl, sec-butyl or tertbutyl, and the various isomeric pentyl, hexyl, heptyl and octyl radicals.

Suitable as haloalkyl are alkyl groups which are mono- or polysubstituted by halogen, halogen specifically being fluorine, chlorine, bromine or iodine. Preferred amongst these alkyl groups which are mono- or polysubstituted by halogen are alkyl groups which are mono- to trisubstituted by halogen, in particular fluorine, chlorine or bromine, for example fluoromethyl, difluoromethyl, trifluoromethyl, chloromethyl, dichloromethyl, trichloromethyl, difluorchloromethyl, 2-fluoroethyl, 2-chloroethyl, 2,2,2-trifluoroethyl, 2,2,2-trichloroethyl; preferably 2-fluoro-n-propyl and 3-fluoro-n-propyl.

Alkoxyalkoxy is, for example, methoxymethoxy, ethoxymethoxy, methoxyethoxy, ethoxyethoxy, methoxypropyloxy or ethoxypropyloxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy; preferably difluoromethoxy, trifluoromethoxy and 2-chloroethoxy.

Suitable as alkenyl groups are straight-chain or branched alkenyl groups, for example allyl, methallyl, but-2-en-1-yl, 3-pentenyl or 2-hexenyl.

Within the scope of the present invention, the alkenyl and alkynyl groups which are bonded to oxygen are, as a rule, bonded via a saturated carbon atom.

Suitable as alkenyloxy groups are straight-chain or branched alkenyloxy groups, for example allyloxy, methallyloxy, but-2-en-1-yloxy, 3-pentenyloxy or 2-hexenyloxy; preferably allyloxy.

Suitable as alkynyloxy groups are straight-chain or branched alkynyloxy groups, for example propargyloxy, 1-methylpropargyloxy, 3-butynyloxy, 2openrtynyloxy or 2-hexynyloxy. Propargyloxy is preferred.

Suitable as cycloalkyloxy are, for example, cyclobutyloxy, cyclopentyloxy or cyclohexyloxy; preferably cyclopentyloxy and cyclohexyloxy.

Suitable as cycloalkylalkoxy groups are, for example, cyclopropylmethyloxy, cyclobutylmethyloxy, cyclopentylmethyloxy, cyclohexylmethyloxy, cyclopropylethyloxy, cyclopentylethyloxy oder cyclohexylethyloxy; preferably cyclopropylmethyloxy.

Suitable as cycloalkyl-substituted alkyl are, for example, cyclopropylmethyl, cyclobutylmethyl, cyclopentylmethyl, cyclohexylmethyl, cyclopropylethyl or cyclohexylethyl; preferably cyclohexylmethyl.

The compounds of the formulae I and II can form salts in which the hydrogen of the —SO$_2$—NH group in the compound of the formula I, or the hydrogen of the radical R$_7$ in the compound of the formula II, is replaced by an agriculturally suitable cation. Examples of these salts are metal salts, in particular alkali metal salts in the case of the compounds of the formula II (R$_7$ hydrogen) or alkali metal salts or alkaline earth metal salts in the case of the compounds of the formula I, or else ammonium salts or salts with organic amines. Salt formation can also be effected by an addition reaction of a strong acid with the pyrimidine or triazine moiety of the compounds of the formula I, and with the pyrazole moiety of the compounds of the formula II. Acids which are suitable for this purpose are hydrochloric acid, hydrobromic acid, sulfuric acid or nitric acid.

Examples of amines which are suitable for the formation of ammonium cations are ammonia as well as primary, secondary and tertiary $C_1$–$C_4$alkylamines, $C_1$–$C_4$hydroxyalkylamines and $C_2$–$C_4$alkoxyalkylamines, for example methylamine, ethylamine, n-propylamine, iso-propylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methylethylamine, methyl-iso-propylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, dion-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2oamine, n-pentenyl-2-amine, 2,3-dimethylbutenyl-2-amine, di-butenyl-2-amine, n-hexenyl-2-amine, propylenediamine, diethanolamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines, for example pyridine, quinoline, iso-quinoline, morpholine, piperidine, pyrrolidine, indoline, quinuclidine and azepine; primary arylamines, for example anilines, methoxyanilines, ethoxyanilines, o,m,p-toluidines, phenylenediamines, benzidines, naphthylamines and o,m,p-chloroanilines; but in particular triethylamine, iso-propylamine and di-iso-propylamine.

Compounds of the formula I or salts thereof which are preferred for use in the composition according to the invention are those of the formula Ia

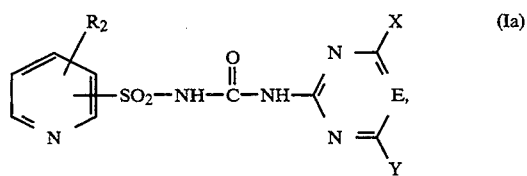

in which R$_2$, X, Y and E are as defined in formula I; in particular those of the formula Ib

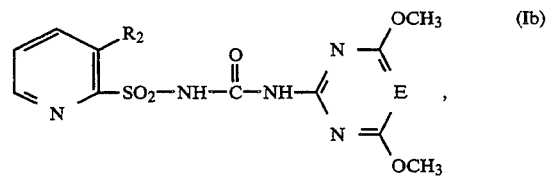

in which R$_2$ and E are as defined in formula I.

Other compounds of the formula I or salts thereof which are preferred for use in the composition according to the invention are those of the formula Ic

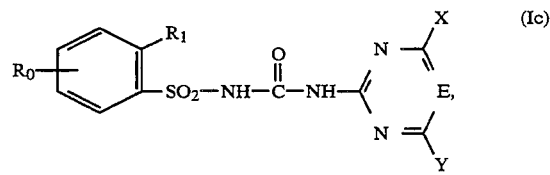

in which R$_0$, R$_1$, X, Y and E are as defined in formula I; in particular those of the formula Id

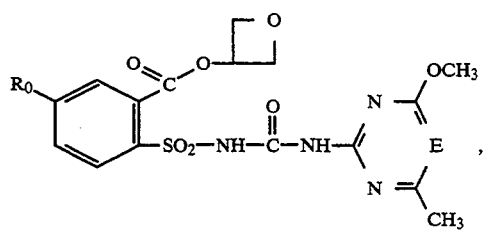

(Id)

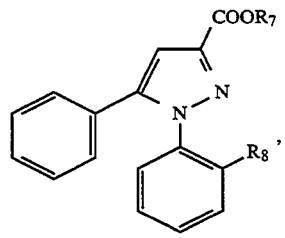

(IIa)

in which $R_0$ is hydrogen or fluorine and E is the methine group or nitrogen.

Compounds of the formula I or salts thereof which are especially preferred for use in the composition according to the invention are those in which Q is a radical

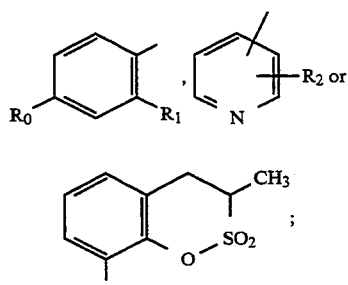

$R_0$ is hydrogen or halogen, in particular fluorine; $R_1$ is $C_1$–$C_3$monofluoroalkyl, difluoromethoxy, propargyloxy, ethynynyl,

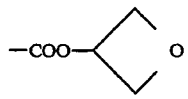

or a radical

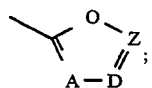

A and Z independently of one another are nitrogen or methine; D is nitrogen, methine or methylmethine; $R_2$ in the 2- or 3-position, alternating with the position of the —$SO_2NHCO$ group, is $C_1$- or $C_2$haloalkoxy, cyclopropylmethyleneoxy, $COOR_4$ or $NR_5R_6$; $R_4$ is methyl or 3-oxetanyl; $R_5$ is hydrogen, methyl or ethyl; $R_6$ is hydrogen, methyl, ethyl, —CHO, —$COCH_3$ or —$COC_2H_5$; X and Y independently of one another are methyl, methoxy, ethoxy or cyclopropyl; and E is nitrogen or the methine group.

Preferred compounds of the formula II for use in the composition according to the invention, in particular in the case of those compositions which comprise the compounds of the formula I containing the substituents which have been mentioned above as being preferred and particularly preferred, are 1,5-diphenylpyrazole-3-carboxylic acid derivatives of the formula IIa in which $R_7$ and $R_8$ are as defined in formula II.

Particularly preferred compounds of the formula IIa are those of the formula IIb

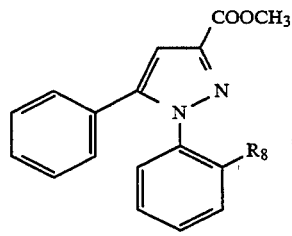

(IIb)

in which $R_8$ is as defined in formula II.

Especially preferred compounds of the formula II are those in which $R_7$ is hydrogen, $C_1$–$C_8$alkyl, methallyl, cyclohexylmethylenyl, sodium, triethylammonium or iso-propylammonium; $R_8$ is hydrogen or halogen; $R_9$ is hydrogen or chlorine; and $R_{10}$ is hydrogen, fluorine or chlorine.

An especially preferred individual compound from within the scope of the formula II is the compound of the formula IIc

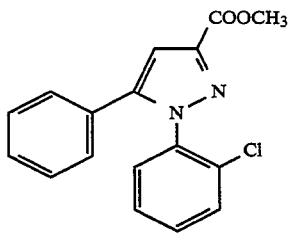

(IIc)

An especially preferred composition according to the invention comprises, as herbicide of the formula I, N-[2-((3-oxetanyl)oxycarbonyl)phenylsulfonyl]-N'-(4-methyl-6-methoxypyrimidin-2-yl)urea (compound of the formula Id in which $R_0$ is hydrogen and E is methine) and, as safener, a compound selected from amongst:

1-(2-chlorophenyl)-3-methoxycarbonyl-5-phenylpyrazole;

1-(2,4-dichlorophen yl)-3-methoxycarbonyl-5-phenylpyrazole;

1-(2-chlorophenyl)-3-benzyloxycarbonyl-5-phenylpyrazole;

1-(2-chlorophenyl)-3-methoxycarbonyl-5-(2,4-dichlorophenyl)pyrazole; or 1-(2-chlorophen yl)-3-methoxycarbon yl-5-( 2-fluorophenyl)pyrazole.

An especially preferred composition according to the invention comprises, as safener, 1-(2-chlorophenyl)-3-methoxycarbonyl-5-phenylpyrazole and, as herbicide from within the scope of the formula I:

N-[2-(cyclopropylmethylenoxy)-3-pyridylsulfonyl]-N'-(4,6-dimethoxypyrimidin-2-yl)urea;

N-[3-(cyclopropylmethylenoxy)-2-pyridylsulfonyl]-N'-(4,6-dimethoxypyrimidin-2-yl)urea;

N-[3-dimethylamino-2-pyridylsulfonyl]-N'-(4,6-dimethoxypydmidin-2-yl)urea;

N-[2-dimethylamino-3-pyridylsulfonyl]-N'-(4-methyl-6-methoxypyrimidin-2-yl)urea:

N-[3-dime thylamino-2-pyri dylsulfonyl]-N'-( 4-methyl-6-methoxypyrimidin-2-yl)urea;

N-[2-((3-oxetanyl)oxycarbonyl)phenylsulfonyl ]-N'-(4,6-dimethylpyrimidin-2-yl)urea;

N-[2-((3-oxetanyl)oxycarbonyl)phenylsulfonyl ]-N'-(4-methyl-6-methoxypyrimidin-2-yl)urea;

N-[2-((3-oxetanyl)oxycarbonyl)phenylsulfonyl]-N'-(4,6-dimethoxypyrimidin-2-yl)urea;

N-[3-difluoromethoxy-2-pyridylsulfonyl]-N'-(4-methyl-6-methoxypyrimidin-2-yl)urea;

N-[3-((3-oxetanyl)oxycarbonyl)-2-pyridylsulfonyl]-N'-(4,6-dimethoxypyrimidin-2-yl)urea; or N-[2-((3-oxetanyl)oxycarbonyl)-4-fluoro-phenylsulfonyl]-N'-(4-methyl-6-methoxypyrimidin-2-yl)urea.

The preparation of the pyridylsulfonylureas of the formula Ia'

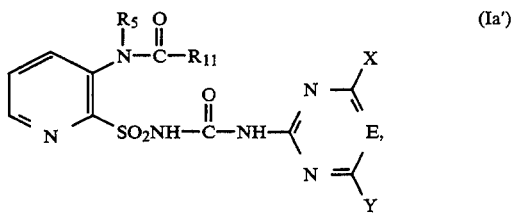

in which $R_5$, $R_{11}$, X, Y and E are as defined in formula I is effected in analogy to known processes and comprises reacting a pyridylsulfonamide of the formula III

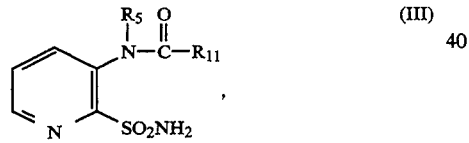

in which $R_5$ and $R_{11}$ are as defined in formula I with an n-pyrimidinylcarbamate of the formula IV

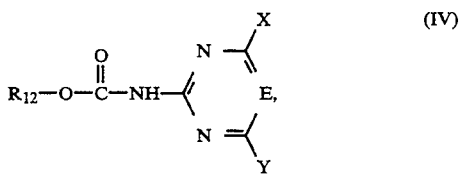

in which X, Y and E are as defined in formula I and $R_{12}$ is $C_1$–$C_4$alkyl or phenyl which can be substituted by $C_1$–$C_4$alkyl or halogen, in the presence of a base.

The reactions to give compounds of the formula Ia' are advantageously effected in aprotic, inert organic solvents. Such solvents are hydrocarbons such as benzene, toluene, xylenes or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as dimethylformamide, diethylfonnamide or N-methylpyrrolidinone. The reaction temperatures are preferably between —20° and 120° C.

As a rule, the reactions proceed slightly exothermally and they can be carried out at room temperature. To shorten the reaction time or else to start up the reaction, it is expedient to heat the reaction mixture briefly up to its boiling point. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. Bases which can be used alternatively are inorganic bases such as hydrides, for example sodium hydride or calcium hydride; hydroxides, for example sodium hydroxide and potassium hydroxide; carbonates, for example sodium carbonate and potassium carbonate; or hydrogen carbonates, for example potassium hydrogen carbonate and sodium hydrogen carbonate.

The end products of the formula Ia' can be isolated by concentration and/or evaporation of the solvent and purified by recrystallisation or trituration of the solid residue in solvents in which they are not readily soluble, such as ethers, aromatic hydrocarbons or chlonnated hydrocarbons.

The intermediates of the formulae III and IV are known and can be prepared analogously to known processes. Processes for the preparation of N-pyrimidinylcarbamates of the formula IV are described, for example, in EP-A-0 101 670.

Compounds of the formula III can be prepared analogously to the processes described in EP-A-0 314 505 and EP-A-0 459 949.

For example, a compound of the formula V

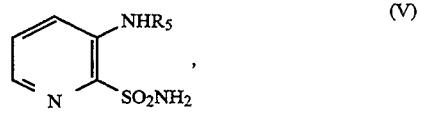

in which $R_5$ is as defined in formula I can be converted into the compound of the formula III using the acylating agent of the formula VI

in which $R_{11}$ is as defined in formula I and Z is halogen, $R_{11}O$— or a conventional leaving group, in the presence of a base. Such reactions are described, for example, in Farmaco Ed. scient. 12, 392 (1957). The compounds of the formula V are known and can be prepared by known methods which are disclosed, for example, in EP-A-0 459 949.

The sulfonylurea herbicides of the formula I are known, and their preparation is described, for example, in U.S. Pat. Nos. 4,544,401, 4,618,363, EP-A-0 044 807, EP-A-0 099 339, EP-A-0 102 925, EP-A-0 103 543, EP-A-0 120 814, EP-A-0 145 664 and EP-A-0 459 949.

The 1,5-diphenylpyrazole-3-carboxylic acid derivatives of the formula II are known and their preparation is described, for example, in EP-A-0 268 554.

Herbicides of the formula I which are particularly suitable for the use according to the invention are described in Tables 1, 2 and 3 below.

TABLE 1

Compounds of the formula Ic (Ic)

Structure: $R_0$-substituted phenyl (positions 1,2,3,4) with $R_1$ at position 2, bearing -SO$_2$NH-C(=O)-NH-C(=N-)(N=) pyrimidine/triazine ring with X, Y, E substituents.

| Comp. No. | R$_1$ | R$_0$ | X | Y | E |
|---|---|---|---|---|---|
| 1.01 | —OCHF$_2$ | H | —OCH$_2$ | —OCH$_3$ | CH |
| 1.02 | —COO-(oxetanyl) | H | —CH$_3$ | —OCH$_3$ | CH |
| 1.03 | —COO-(oxetanyl) | H | —CH$_3$ | —CH$_3$ | CH |
| 1.04 | —COO-(oxetanyl) | H | —OCH$_3$ | —OCH$_3$ | CH |
| 1.05 | —COOCH$_3$ | H | —OC$_2$H$_5$ | (cyclopropyl) | N |
| 1.06 | —OCH$_2$C≡CH | H | —OCH$_3$ | —CH$_3$ | N |
| 1.07 | —CH$_2$CH$_2$CH$_2$—F | H | —OCH$_3$ | —CH$_3$ | CH |
| 1.08 | —CH$_2$CH$_2$—F | H | —OCH$_3$ | —CH$_3$ | N |
| 1.09 | —CH$_2$—CH(CH$_3$)—F | H | —OCH$_3$ | —CH$_3$ | N |
| 1.10 | —C≡CH | H | —OCH$_3$ | —CH$_3$ | N |
| 1.11 | —C≡CH | H | —OCH$_3$ | —CH$_3$ | CH |
| 1.12 | —C≡CH | H | —OCH$_3$ | —OCH$_3$ | CH |
| 1.13 | (methyl-oxadiazolyl with CH$_3$) | H | —OCH$_3$ | —OCH$_3$ | CH |
| 1.14 | (methyl-isoxazolyl) | H | —OCH$_3$ | —OCH$_3$ | CH |
| 1.15 | (methyl-oxadiazinyl) | H | —OCH$_3$ | —OCH$_3$ | CH |
| 1.16 | —COO-(oxetanyl) | 4-F | —OCH$_3$ | —CH$_3$ | CH |

TABLE 2

Compounds of the formula Ia (Ia)

Structure: pyridine ring with $R_2$ substituent, bearing -SO$_2$NH-C(=O)-NH-C(=N-)(N=) pyrimidine/triazine ring with X, Y, E substituents.

| Comp. No. | Position —SO$_2$NHCO— | R$_2$ | X | Y | E |
|---|---|---|---|---|---|
| 2.01 | 3 | 2-N(CH$_3$)$_2$ | —OCH$_3$ | —OCH$_3$ | CH |
| 2.02 | 3 | 2-O—CH$_2$-(cyclopropyl) | —OCH$_3$ | —OCH$_3$ | CH |
| 2.03 | 2 | 3-O—CH$_2$-(cyclopropyl) | —OCH$_3$ | —OCH$_3$ | CH |
| 2.04 | 2 | 3-OCHF$_2$ | —OCH$_3$ | —OCH$_3$ | CH |
| 2.05 | 2 | 3-OCHF$_2$ | —OCH$_3$ | —OCH$_3$ | CH |
| 2.06 | 2 | 3-N(CH$_3$)$_2$ | —OCH$_3$ | —OCH$_3$ | CH |
| 2.07 | 2 | 3-NHC$_2$H$_5$ | —OCH$_3$ | —OCH$_3$ | CH |
| 2.08 | 2 | 3-N(CH$_3$)$_2$ | —OCH$_3$ | —CH$_3$ | CH |
| 2.09 | 2 | 3-COO-(oxetanyl) | —OCH$_3$ | —OCH$_3$ | CH |

TABLE 2-continued

Compounds of the formula Ia (Ia)

| Comp. No. | Position —SO₂NHCO— | $R_2$ | X | Y | E |
|---|---|---|---|---|---|
| 2.10 | 2 | 3-OCH₂CH₂Cl | —OCH₃ | —OCH₃ | CH |

TABLE 3

Compounds of the formula

| Comp. No. | $R_3$ | X | Y | E |
|---|---|---|---|---|
| 3.01 | —CH₃ | —CH₃ | —CH₃ | CH |

Safeners of the formula II which are particularly suitable for the use according to the invention are listed in Table 4 below.

TABLE 4

Compounds of the formula II (II)

| Comp. No. | $R_8$ | $R_9$ | $R_{10}$ | $R_7$ |
|---|---|---|---|---|
| 4.01 | Cl | H | H | —CH₃ |
| 4.02 | Cl | H | H | H |
| 4.03 | F | H | H | —CH₃ |
| 4.04 | Cl | H | 3-F | —CH₃ |
| 4.05 | Br | H | H | —CH₃ |
| 4.06 | H | H | H | —CH₃ |
| 4.07 | Cl | H | H | —CH₂—C(CH₃)=CH₂ |
| 4.08 | Cl | H | H | —C₄H₉(n) |
| 4.09 | Cl | H | H | —CH(CH₃)(C₅H₁₁-n) |
| 4.10 | Cl | H | H | —C₈H₁₇(n) |
| 4.11 | H | H | H | —C₂H₅ |
| 4.12 | Cl | Cl | H | —CH₃ |
| 4.13 | Cl | H | 3-Cl | —CH₃ |
| 4.14 | Cl | H | H | HN⁺(C₂H₅)₃ |
| 4.15 | Cl | H | H | H₃N⁺—CH(CH₃)₂ |
| 4.16 | Cl | H | H | Na⁺ |
| 4.17 | Cl | H | H | —CH₂-cyclohexyl(H) |
| 4.18 | Cl | Cl | 2-Cl | —CH₃ |
| 4.19 | Cl | H | 2-F | —CH₃ |

The invention also relates to a method for the selective control of weeds in crops of useful plants, which comprises treating the useful plants, the seeds or cuttings thereof or the area on which they are grown, simultaneously or independently of one another with a herbicidally effective amount of the sulfonylurea of the formula I and a herbicide-antagonistically effective amount of a 1,5-diphenylpyrazole-3-carboxylic acid derivative of the formula II.

Suitable crop plants which can be protected against the damaging effect of the abovementioned herbicides by the 1,5-diphenylpyrazole-3-carboxylic acid derivatives of the formula II are in particular those which are important in the food or textile sector, for example sugar cane and, in particular, cultivated millets, maize, rice and other cereal species (wheat, rye, barley, oats), but especially wheat and barley.

The weeds to be controlled can be monocotyledon as well as dicotyledon weeds.

Suitable crops or parts of these plants are, for example, those mentioned above. The areas on which they are grown are the areas of soil on which the crop plants are growing already or which have been sown with the seed of these crop plants, as well as the soils intended for the cultivation of these crop plants.

Depending on the intended purpose, a safener or antidote of the formula II can be used for pretreating the seed of the crop plant (dressing of the seed or treatment of the cuttings) or incorporated into the soil before or after sowing. Alternatively, it can be applied, as pure active ingredient or together with the herbicide, before or after emergence of the plants. The treatment of the plant or of the seed with the safener can therefore be carried out essentially independently of the time of application of the phytotoxic chemical. However, the treatment of the plant can also be carded out by simultaneous application of phytotoxic chemical and safener (tank mix). Preemergence treatment includes treatment of the area under cultivation before sowing (ppi=preplant incorporation) as well as treatment of the areas under cultivation on which seed has been sown, but growth of the plants has not yet taken place.

The amount of safener to be applied relative to the herbicide depends largely on the method of application. The ratio of safener to herbicide in the case of field treatment, either using a tank mix with a combination of safener and herbicide or separate application of safener and herbicide, is, as a rule, 1:100 to 10:1, preferably 1:20 to 1:1, and in particular 1:1. In contrast, far smaller amounts of safener relative to the amount of herbicide applied per hectare of area under cultivation are required in the case of seed dressing.

As a rule, 0.001 to 5.0 kg of safener/ha, preferably 0.01 to 0.5 kg of safener/ha, are applied in the case of field treatment.

The application rates of herbicide are, as a rule, between 0.001 to 4 kg/ha, but preferably between 0.05 and 2 kg/ha.

As a rule, 0.001 to 10 g of safener/kg of seed, preferably 0.05 to 2 g of safener/kg of seed, are applied in the case of seed dressing. If the safener is applied in liquid form shortly before sowing in the form of seed soaking, it is expedient to use safener solutions comprising the active ingredient at a concentration of 1 to 10,000, preferably 100 to 1000 ppm.

For application, the compounds of the formula II, or combinations of compounds of the formula II together with the herbicides to be antagonised, are expediently employed together with the auxiliaries conventionally used in the art of formulation and they are therefore processed in a known manner to give, for example, emulsion concentrates, spreadable pastes, directly sprayable or dilutable solutions, dilute emulsions, wettable powders, soluble powders, dusts, granules and also encapsulations, for example in polymeric substances. The methods of application such as spraying, atomising, dusting, scattering, brushing on or pouting, as well as the type of composition to be used, are selected to suit the intended aims and the prevailing circumstances.

The formulations, i.e. the compositions, preparations or formulations comprising the active ingredient of the formula II or a combination of active ingredient of the formula II with herbicide to be antagonised of the formula I with or without a solid or liquid additive, are prepared in a known manner, for example by intimately mixing and/or grinding the active ingredients with extenders, for example with solvents, solid carders and, if desired, surface-active compounds (surfactants).

The following are possible as solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols, as well as their ethers and esters such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or dimethylformamide, and also epoxidised or unepoxidised vegetable oils, such as epoxidised coconut oil or soya oil; or water.

Solid carriers which are used, for example for dusts and dispersible powders, are, as a rule, ground natural minerals such as calcite, talc, kaolin, montmorillonite or attapulgite. To improve the physical properties, it is also possible to add highly-disperse silica or highly-disperse absorptive polymers. Possible. particulate, adsorptive carriers for granules are either porous types, for example pumice, brick grit, sepiolite or bentonite, or non-sorptive carrier materials, such as calcite or sand. Moreover, a large number of pregranulated materials of inorganic or organic nature such as, in particular, dolomite or comminuted plant residues, can be used.

Suitable surface-active compounds are non-ionic, cationic and/or anionic surfactants having good emulsifying, dispersing and wetting properties, depending on the nature of the active ingredient of the formula II to be formulated as well as, .if appropriate, the herbicide of the formula I to be antagonised. Surfactants are also to be understood as meaning mixtures of surfactants.

Suitable anionic suffactants can be so-called water-soluble soaps as well as water-soluble synthetic surface-active compounds.

Suitable soaps which may be mentioned are the alkali metal salts, alkaline earth metal salts or substituted or unsubstituted ammonium salts of higher fatty acids ($C_{10}$-$C_{22}$), for example the sodium or potassium salts of oleic or stearic acid, or of natural mixtures of fatty acids which can be obtained, for example, from coconut oil or tallow oil. Mention must also be made of the fatty acid methyl tauffnates.

However, so-called synthetic surfactants are used more frequently, in particular fatty sulfonates, fatty sulfates, sulfonated benzimidazole derivatives or alkylarylsulfonates.

The fatty sulfonates or fatty sulfates are, as a rule, in the form of alkali metal salts, alkaline earth metal salts or unsubstituted or substituted ammonium salts and have an alkyl radical having 8 to 22 C atoms, alkyl also including the alkyl moiety of acyl radicals, for example the sodium or calcium salt of ligninsulfonic acid, of the dodecylsulfuric ester or of a fatty alcohol sulfate mixture prepared with natural fatty acids. This group also includes the salts of the sulfuric esters and sulfonic acids of fatty alcohol/ethylene oxide adducts. The sulfonated benzimidazole derivatives preferably contain 2 sulfonyl groups and one fatty acid radical having 8 to 22 C atoms. Examples of alkylarylsulfonates are the sodium, calcium or triethanolamine salts of dodecylbenzenesulfonic acid, of dibutylnaphthalenesulfonic acid or of a naphthalenesulfonic acid/formaldehyde condensation product.

Other suitable compounds are the corresponding phosphates, for example salts of the phosphoric ester of a p-nonylphenol/(4–14)-ethylene oxide adduct, or phospholipids.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other non-ionic surfactants which are suitable are the water-soluble polyethylene oxide adducts with polypropylene glycol, ethylenediaminopolypropylene glycol and alkylpolypropylene glycol which have 1 to 10 carbon atoms in the alkyl chain and which contain 20 to 250 ethylene glycol ether groups and 10 to 100 propylene glycol ether groups. As a rule, the abovementioned compounds contain 1 to 5 ethylene glycol units per propylene glycol unit.

Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Other suitable substances are fatty acid esters of polyoxyethylene sorbitan, such as polyoxyethylene sorbitan trioleate.

The cationic surfactants are, in particular, quaternary ammonium salts which contain at least one alkyl radical having 8 to 22 C atoms as N substituent and which have lower halogenated or free alkyl, benzyl or lower hydroxyalkyl radicals as further substituents.

The salts are preferably in the form of halides, methylsulfates or ethylsulfates, for example stearyltrimethylammonium chloride or benzyldi(2-chloroethyl)ethylammonium bromide.

The surfactants conventionally used in the art of formulation are described, inter alia, in the following publications:

"McCutcheon's Detergents and Emulsifiers Annual" MC Publishing Corp., Ridgewood N.J., 1981. Stache, H., "Tensid-Taschenbuch" [Suffactant Guide], Carl Hanser Verlag, Munich/Vienna, 1981.

As a rule, the agrochemical preparations comprise 0.1 to 99 percent by weight, in particular 0.1 to 95% by weight, of active ingredient of the formula II or active ingredient mixture antidote/herbicide, 1 to 99.9% by weight, in particular 5 to 99.8% by weight, of a solid or liquid additive and 0 to 25%:by weight, in particular0.1 to 25% by weight, of a surfactant.

While concentrated compositions are more preferred as commercially available goods, the end user uses, as a rule, dilute compositions.

The compositions can also comprise further additives such as stabilisers, defoamers, viscosity regulators, binders, tackifiers as well as fertilisers and other active ingredients for achieving specific effects.

Various methods and techniques are suitable for using compounds of the formula II, or compositions containing them, for protecting crop plants against damaging effects of herbicides of the formula I, for example the following:

i) Seed dressing a) The seeds are dressed using an active ingredient of the formula II formulated as a wettable powder, by shaking in a container until the seed surface is coated uniformly (dr3, seed dressing). Approximately 1 to 500 g of active ingredient of the formula II (4 g to 2 kg of wettable powder) are used per 100 kg of seed.

b) The seeds are dressed with an emulsion concentrate of the active ingredient of the formula II, using method a) (wet seed dressing).

c) The seeds are dressed by immersion in a liquor containing 100–1000 ppm of active ingredient of the formula II over a period of 1 to 72 hours, which, if desired, is followed by drying the seeds (seed soaking).

Naturally, seed dressing or treatment of the germinated seedling are the preferred methods of application since treatment with active ingredient is directed entirely at the target crop. As a rule, 1 to 1000 g of antidote, preferably 5 to 250 g of antidote, are used per 100 kg of seed, it being possible to deviate from the limit concentrations given in both directions, depending on the method chosen which also makes possible the addition of other active ingredients or micronutrients (repeated seed dressing).

ii) Application with the aid of a tank mix

A liquid preparation of a mixture of antidote and herbicide (ratio by weight between 10:1 and 1:100) is used, and the application rate of herbicide being 0.01 to 5.0 kg per hectare. Such a tank mix is applied before or after sowing.

iii) Application in the seed furrow

The antidote in the form of an emulsion concentrate, wettable powder or granules is incorporated into the open seed furrow in which seed has been sown, whereupon the seed furrow is covered and the herbicide is applied preemergence in the usual manner.

iv) Controlled release of active ingredient

The dissolved active ingredient of the formula II is applied to mineral granule carriers or polymerised granules (urea/formaldehyde) and allowed to dry. If desired, a coating can be applied (coated granules), which permits slow release of the active ingredient over a certain period.

Preparation Examples

Example H1:Preparation of 3-(N-methyl-N-acetylamino)pyridin-2-ylsulfonamide

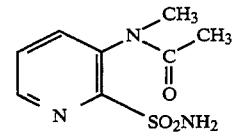

0.89 ml of pyridine and 0.82 ml of acetyl bromide are added in succession at room temperature to a solution of 1.87 g of 3-N-methylaminopyridin-2-ylsulfonamide in 40 ml of dry acetonitrile. After 30 minutes, a further 0.3 ml of acetyl bromide is added, the mixture is stirred for a further hour, and 0.32 ml of pyridine is then added. The reaction mixture is stirred for 30 minutes and the product 3-(N-methyl-N-acetylamino)pyridin-2-ylsulfonamide is then filtered off; m.p. 181°–185° C.

Example H2: Preparation of N-(N-methyl-N-acetylamino)pyridin-2-ylsulfonyl-N'-(4-methoxy-6-methylpyrimidin-2-yl)urea

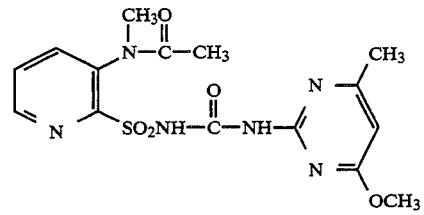

2.18 ml of 1,5-diazabicyclo[5.4.0]undec-5-ene and 3.89 g of N-(4-methoxy-6-methylpyrimidin-2-yl)phenyl carbamate are added in succession to a solution of 3.07 g of 3-(N-methyl-N-acetylamino)pyridin-2-ylsulfonamide in 50 ml of acetonitrile. The reaction mixture is stirred for 45 minutes and then concentrated in vacuo, the oily residue is triturated with 10 ml of 2N hydrochloric acid, and the mixture is subsequently diluted with 10 ml of water. The crystalline product is filtered off and subsequently washed with water and diethyl ether. 5.25 g of N-(N-methyl-N-acetylamino)pyridin2- ylsulfonyl-N'-(4-methoxy-6-methylpyrimidin-2-yl)urea with a melting point of 178°–180° C. are obtained.

Formulation examples of liquid active ingredients of the formula II or mixtures thereof with a herbicide of the formula I (% = percent by weight)

| 1. Emulsion concentrates | a) | b) | c) |
|---|---|---|---|
| Active ingredient mixture | 25% | 40% | 50% |
| Calcium dodecylbenzenesulfonate | 5% | 8% | 6% |
| Castor oil polyethylene glycol ether (36 moles of EO) | 5% | — | — |
| Tributylphenol polyethylene glycol ether (30 moles of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| 2. Solutions | a) | b) | c) | d) |
|---|---|---|---|---|
| Active ingredient mixture | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidised coconut oil | — | — | 1% | 5% |
| Petroleum spirit (boiling range 160–190°) | — | — | 94% | — |

The solutions are suitable for use in the form of microdrops.

| 3. Granules | a) | b) |
|---|---|---|
| Active ingredient mixture | 5% | 10% |
| Kaolin | 94% | — |
| Highly-disperse silica | 1% | — |
| Attapulgite | — | 90% |

The active ingredient is dissolved in methylene chloride, the solution is sprayed onto the carder, and the solvent is subsequently evaporated in vacuo.

| 4. Dusts | a) | b) |
|---|---|---|
| Active ingedient mixture | 2% | 5% |
| Highly-disperse silica | 1% | 5% |
| Talc | 97% | — |
| Kaolin | — | 90% |

Ready-for-use dusts are obtained by intimately mixing the carriers with the active ingredient.

Formulation examples of solid active ingredients of the formula II or mixtures thereof with a herbicide of the formula I (% = percent by weight)

| 5. Wettable powders | a) | b) | c) |
|---|---|---|---|
| Active ingredient mixture | 25% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 moles of EO) | — | 2% | — |
| Highly-disperse silica | 5% | 10% | 10% |
| Kaolin | 62% | 27% | — |

The active ingredient is mixed thoroughly with the additives and the mixture is ground thoroughly in a suitable mill. This gives wettable powders which can be diluted with water to give suspensions of any desired concentration.

| 6. Emulsion concentrate | |
|---|---|
| Active ingredient mixture | 10% |
| Octylphenol polyethylene glycol ether (4–5 moles of EO) | 3% |
| Calcium dodecylbenzenesulfonate | 3% |
| Castor oil polyglycol ether (35 moles of EO) | 4% |
| Cyclohexanone | 30% |
| Xylene mixture | 50% |

Emulsions of any desired concentration can be prepared from this concentrate by dilution with water.

| 7. Dusts | a) | b) |
|---|---|---|
| Active ingredient mixture | 5% | 8% |
| Talc | 95% | — |
| Kaolin | — | 92% |

Ready-for-use dusts are obtained by mixing the active ingredient with the carders and grinding the mixture in a suitable mill.

| 8. Extruder granules | |
|---|---|
| Active ingredient mixture | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| 9. Coated granules | |
|---|---|
| Active ingredient mixture | 3% |
| Polyethylene glycol (MW 200) | 3% |
| Kaolin | 94% |

In a mixer, the kaolin which has been moistened with polyethylene glycol is coated uniformly with the finely ground active ingredient. Dust-free coated granules are obtained in this manner.

| 10. Suspension concentrate | |
|---|---|
| Active ingredient mixture | 40% |
| Ethylene glycol | 10% |
| Nonylphenol polyethylene glycol ether (15 moles of EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. In this manner, a suspension concentrate is obtained from which suspensions of any desired concentration can be prepared by dilution with water.

Biological examples

The capability of the compounds of the formula II to protect crop plants against the phytotoxic effect of powerful herbicides can be seen from the examples which follow.

Example B 1: Postemergence phytotoxic effects of the herbicide N-[2-((3-oxetanyl)oxycarbonyl)phenylsulfonyl]-N'-(4-methoxy-6-methylpyrimidin-2-yl)urea (Compound No. 1.02) and of the mixtures of herbicide with safener of the formula II on wheat and barley Wheat and barley are grown in plastic pots under greenhouse conditions until they have reached the 4-leaf stage. At this stage, the herbicide N-[2-((3-oxetanyl)oxycarbonyl)phenylsulfonyl]-N'-(4-methoxy-6-methylpyrimidin-2-yl)urea (Compound No. 1.02), on the one hand as pure active ingredient, as well as the mixtures of the herbicide with the substances to be tested as safener of the formula II are applied to the test plants. Application is effected in the form of an aqueous suspension prepared with a suspension concentrate (Formulation Example 10) of the test substances using 500 l of water/ha. The application rates are 15 g/ha in the case of the herbicide and 250 g/ha in the case of the compounds of the formula II to be tested as safener. 22 days after application, the test is evaluated using a percentage scale. 100% means that the test plant has died, 0% means no phytotoxic effect. The results obtained are shown in Table B 1. The results demonstrate that damage to wheat and barley caused by the herbicide can be markedly reduced with the safeners in Table 4.

Identical results are obtained when the abovementioned aqueous suspension is prepared with an emulsion concentrate (Formulation Example 1), a solution (Formulation Example 2), granules (Formulation Example 3), dusts (Formulation Examples 4 and 7), wettable powder (Formulation Example 5), emulsion concentrate (Formulation Example 6) or extruder granules or coated granules (Formulation Examples 8 and 9).

TABLE B1

Postemergence phytotoxic effects of the herbicide N-[2-((3-oxetanyl)oxycarbonyl)phenylsulfonyl]-N'-(4-methoxy-6-methyl-pyrimidin-2-yl)urea (Comp. No. 1.02; 15 g/ha) and the mixtures of herbicide with safener (formula II: 250 g/ha) on wheat and barley.

| Herbicide Comp. No. | Safener Comp. No. | Phytotoxic effect in % Wheat | Phytotoxic effect in % Barley |
|---|---|---|---|
| 1.02 | — | 75 | 75 |
| 1.02 | 4.01 | 10 | 45 |
| 1.02 | 4.02 | 25 | 45 |
| 1.02 | 4.03 | 10 | 55 |
| 1.02 | 4.04 | 15 | 65 |
| 1.02 | 4.05 | 15 | 50 |
| 1.02 | 4.06 | 60 | 65 |
| 1.02 | 4.07 | 20 | 70 |
| 1.02 | 4.08 | 10 | 60 |
| 1.02 | 4.09 | 20 | 55 |
| 1.02 | 4.10 | 35 | 65 |
| 1.02 | 4.11 | 45 | 75 |
| 1.02 | 4.12 | 5 | 40 |
| 1.02 | 4.13 | 30 | 50 |
| 1.02 | 4.14 | 20 | 65 |
| 1.02 | 4.15 | 15 | 65 |
| 1.02 | 4.16 | 10 | 60 |
| 1.02 | 4.17 | 10 | 45 |
| 1.02 | 4.18 | 10 | 45 |
| 1.02 | 4.19 | 10 | 45 |

Example B2: Postemergence phytotoxic effects of various herbicidal sulfonylureas of Tables 1, 2 and 3 as pure active ingredients and in the form of mixtures with the safener 1-(2-chlorophenyl)-3-methoxycarbonyl-5-phenylpyrazole (Comp. No. 4.01)

Wheat and barley are grown in plastic pots under greenhouse conditions until they have reached the 4-leaf stage. At this stage, the herbicides listed in Table B2 as pure active ingredients, on the one hand, as well as the mixtures of the herbicides with the safener 1-(2-chlorophenyl)-3-methoxycarbonyl-5-phenylpyrazole (Comp. No. 4.01 ) are applied to the test plants. The application is effected in the form of an aqueous suspension prepared with a suspension concentrate (Formulation Example 10) of the test substances using 500 l of water/ha. The application rate of the safener (Comp. 4.01) is always 125 g/ha, the application rates of the herbicides can be seen in Table B2. 18 days after application, the test is evaluated using a percentage scale: 100% means that the test plant has died, 0% means no phytotoxic effect. The results obtained are shown in Table B2. The results demonstrate that the crop plants wheat and barley can be protected against the phytotoxic effect of the herbicidal test substances by using the safener (Comp. No. 4.01 ).

Identical results are obtained when the abovementioned aqueous suspension is prepared with an emulsion concentrate (Formulation Example 1), a solution (Formulation Example 2), granules (Formulation Example 3), dusts (Formulation Examples 4 and 7), wettable powder (Formulation Example 5), emulsion concentrate (Formulation Example 6) or extruder granules or coated granules (Formulation Examples 8 and 9).

TABLE B2

Postemergence phytotoxic effects of various herbicidal sulfonylureas of Tables 1, 2 and 3 as pure active ingredients and in the form of mixtures with the safener 1-(2-chlorophenyl)-3-methoxycarbonyl-5-phenylpyrazole (Comp. No. 4.01; 125 g/ha).

| Herbicide Comp. No. | g/ha | Safener Comp. No. | Phytotoxic effect in % Wheat | Phytotoxic effect in % Barley |
|---|---|---|---|---|
| 1.01 | 30 | — | 85 | 85 |
|  | 15 | — | 40 | 70 |
|  | 8 | — | 10 | 65 |
| 1.01 | 30 | 4.01 | 55 | 65 |
|  | 15 | 4.01 | 25 | 50 |
|  | 8 | 4.01 | 5 | 40 |
| 1.02 | 30 | — | 65 | 85 |
|  | 15 | — | 45 | 75 |
|  | 8 | — | 20 | 65 |
| 1.02 | 30 | 4.01 | 25 | 70 |
|  | 15 | 4.01 | 5 | 55 |
|  | 8 | 4.01 | 0 | 20 |
| 1.03 | 125 | — | 60 | 85 |
|  | 60 | — | 30 | 75 |
|  | 30 | — | 10 | 60 |
| 1.03 | 125 | 4.01 | 25 | 50 |
|  | 60 | 4.01 | 5 | 30 |
|  | 30 | 4.01 | 0 | 10 |
| 1.04 | 30 | — | 35 | 70 |
|  | 15 | — | 10 | 60 |
|  | 8 | — | 0 | 30 |
| 1.04 | 30 | 4.01 | 0 | 25 |
|  | 15 | 4.01 | 0 | 10 |
|  | 8 | 4.01 | 0 | 0 |
| 1.05 | 125 | — | 90 | 90 |
|  | 60 | — | 75 | 85 |
|  | 30 | — | 60 | 75 |
| 1.05 | 125 | 4.01 | 70 | 80 |
|  | 60 | 4.01 | 45 | 70 |
|  | 30 | 4.01 | 15 | 60 |

TABLE B2-continued

Postemergence phytotoxic effects of various herbicidal sulfonylureas of Tables 1, 2 and 3 as pure active ingredients and in the form of mixtures with the safener 1-(2-chlorophenyl)-3-methoxycarbonyl-5-phenylpyrazole (Comp. No. 4.01; 125 g/ha).

| Herbicide Comp. No. | g/ha | Safener Comp. No. | Phytotoxic effect in % Wheat | Phytotoxic effect in % Barley |
|---|---|---|---|---|
| 1.06 | 500 | — | — | 40 |
|  | 250 | — | — | 25 |
|  | 125 | — | — | 15 |
| 1.06 | 500 | 4.01 | — | 10 |
|  | 250 | 4.01 | — | 5 |
|  | 125 | 4.01 | — | 0 |
| 1.07 | 500 | — | — | 20 |
|  | 250 | — | — | 10 |
|  | 125 | — | — | 5 |
| 1.07 | 500 | 4.01 | — | 5 |
|  | 250 | 4.01 | — | 0 |
|  | 125 | 4.01 | — | 0 |
| 1.16 | 125 | — | — | 80 |
|  | 60 | — | — | 40 |
|  | 30 | — | — | 20 |
|  | 15 | — | — | 10 |
| 1.16 | 125 | 4.01 | — | 20 |
|  | 60 | 4.01 | — | 15 |
|  | 30 | 4.01 | — | 5 |
|  | 15 | 4.01 | — | 0 |
| 2.01 | 125 | — | 40 | 60 |
|  | 60 | — | 20 | 30 |
|  | 30 | — | 5 | 10 |
| 2.01 | 125 | 4.01 | 15 | 25 |
|  | 60 | 4.01 | 5 | 15 |
|  | 30 | 4.01 | 0 | 5 |
| 2.02 | 500 | — | 60 | 40 |
|  | 250 | — | 15 | 20 |
|  | 125 | — | 5 | 10 |
| 2.02 | 500 | 4.01 | 15 | 25 |
|  | 250 | 4.01 | 5 | 10 |
|  | 125 | 4.01 | 0 | 5 |
| 2.03 | 30 | — | 65 | 70 |
|  | 15 | — | 25 | 40 |
|  | 8 | — | 5 | 15 |
| 2.03 | 30 | 4.01 | 30 | 40 |
|  | 15 | 4.01 | 10 | 25 |
|  | 8 | 4.01 | 0 | 5 |
| 2.04 | 30 | — | 25 | 65 |
|  | 15 | — | 5 | 60 |
|  | 8 | — | 0 | 50 |
| 2.04 | 30 | 4.01 | 0 | 30 |
|  | 15 | 4.01 | 0 | 10 |
|  | 8 | 4.01 | 0 | 5 |
| 2.05 | 30 | — | 75 | 90 |
|  | 15 | — | 10 | 75 |
|  | 8 | — | 0 | 60 |
| 2.05 | 30 | 4.01 | 20 | 65 |
|  | 15 | 4.01 | 5 | 25 |
|  | 8 | 4.01 | 0 | 15 |
| 2.06 | 125 | — | 50 | 55 |
|  | 60 | — | 10 | 25 |
|  | 30 | — | 5 | 15 |
| 2.06 | 125 | 4.01 | 10 | 30 |
|  | 60 | 4.01 | 5 | 10 |
|  | 30 | 4.01 | 0 | 5 |
| 2.08 | 250 | — | 85 | 75 |
|  | 125 | — | 60 | 70 |
|  | 60 | — | 25 | 60 |
| 2.08 | 250 | 4.01 | 60 | 45 |
|  | 125 | 4.01 | 25 | 30 |
|  | 60 | 4.01 | 5 | 25 |
| 2.09 | 30 | — | 30 | 50 |
|  | 15 | — | 10 | 15 |
|  | 8 | — | 5 | 5 |
| 2.09 | 30 | 4.01 | 20 | 20 |
|  | 15 | 4.01 | 5 | 5 |
|  | 8 | 4.01 | 0 | 0 |
| 2.10 | 30 | — | 90 | 90 |
|  | 15 | — | 60 | 80 |
|  | 8 | — | 15 | 60 |
| 2.10 | 30 | 4.01 | 90 | 85 |
|  | 15 | 4.01 | 35 | 65 |
|  | 8 | 4.01 | 0 | 40 |
| 3.01 | 30 | — | 90 | 70 |
|  | 15 | — | 60 | 50 |
|  | 8 | — | 10 | 30 |
| 3.01 | 30 | 4.01 | 80 | 40 |
|  | 15 | 4.01 | 40 | 30 |
|  | 8 | 4.01 | 0 | 10 |

What is claimed is:

1. A composition for the selective control of weeds in crops of useful plants, which comprises, besides inert carders and additives, as active ingredient a mixture comprising a) a herbicidally effective amount of a sulfonylurea of the formula I

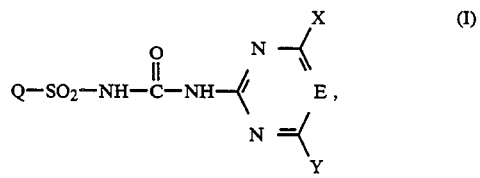

in which Q is a radical

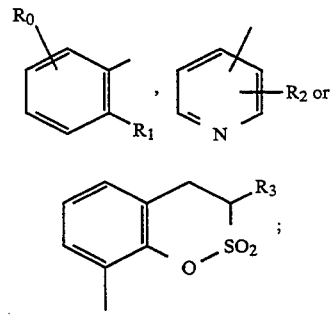

$R_0$ is hydrogen, halogen, methyl or methoxy; $R_1$ is halogen, $C_1$-$C_3$haloalkyl, $C_1$-$C_3$haloalkoxy, $C_1$- or $C_2$alkoxy-$C_1$-$C_3$alkoxy, $C_3$-$C_6$alkenyloxy, $C_3$-$C_6$alkynyloxy, $C_2$-or $C_3$alkynyl,

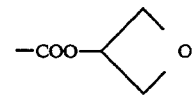

or a radical

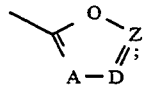

A and Z independently of one another are nitrogen or methine; D is nitrogen, methine or methylmethine; $R_2$ is $C_1$-$C_3$haloalkoxy, $C_7$ or $C_2$alkoxy-$C_1$-$C_3$alkoxy, $C_4$-$C_6$-cycloalkyloxy, $C_3$-$C_6$cycloalkyl-$C_1$-$C_3$alkoxy, —$COOR_4$ or —$NR_5R_6$; $R_4$ is $C_1$-$C_3$alkyl or 3-oxetanyl;

$R_5$ is hydrogen or $C_1$-$C_4$alkyl; $R_6$ is hydrogen, $C_1$-$C_4$alkyl or —$COR_{11}$; $R_{11}$ is hydrogen or $C_1$-$C_6$alkyl; $R_3$ is hydrogen or methyl; X is halogen, methyl, ethyl, methoxy, ethoxy, $C_1$- or $C_2$haloalkoxy, cyclopropyl, —$NHCH_3$ or —$N(CH_3)_2$; Y is methyl, ethyl, methoxy, ethoxy, $C_1$- or $C_2$-haloalkoxy or cyclopropyl; and E is nitrogen or the methine group; and the agrochemically acceptable salts of these compounds, in which D and Z must not simultaneously be nitrogen; and E is the methine group if X is halogen or difluoromethoxy; and b), as safener, a herbicide-antagonistically effective amount of a 1,5-diphenylpyrazole-3-carboxylic acid derivative of the formula II

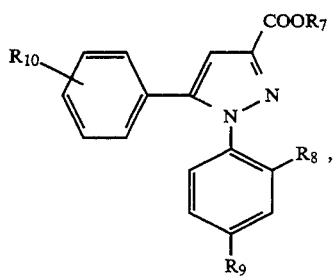

in which $R_7$ is hydrogen, $C_1$-$C_8$alkyl, $C_3$-$C_6$alkenyl, $C_3$-$C_6$cycloalkyl-$C_1$-$C_3$alkyl, or an alkali metal or ammonium cation; and $R_8$, $R_9$ and $R_{10}$ independently of one another are hydrogen or halogen.

2. A composition according to claim 1, which comprises, as herbicide, a compound of the formula Ia

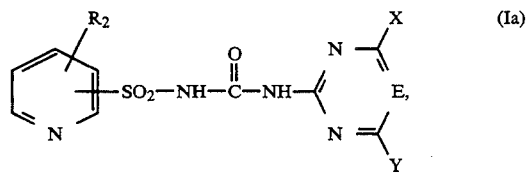

in which $R_2$, X, Y and E are as defined in claim 1.

3. A composition according to any one of claims 1 or 2, which comprises, as herbicide, a compound of the formula Ib

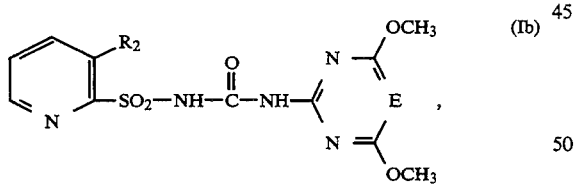

in which $R_2$ is $C_1$-$C_3$haloalkoxy, $C_1$- or $C_2$alkoxy-$C_1$-$C_3$alkoxy, $C_4$-$C_6$cycloalkyloxy, $C_3$-$C_6$cycloalkyl-$C_1$-$C_3$alkoxy, —$COOR_4$ or —$NR_5R_6$; $R_4$ is $C_1$-$C_3$alkyl or 3-oxetanyl; $R_5$ is hydrogen or $C_1$-$C_4$alkyl; $R_6$ is hydrogen, $C_1$-$C_4$alkyl or —$COR_1$; $R_{11}$ is hydrogen or $C_1$-$C_6$alkyl; and E is nitrogen or the methine group.

4. A composition according to claim 1, which comprises, as herbicide, a compound of the formula Ic

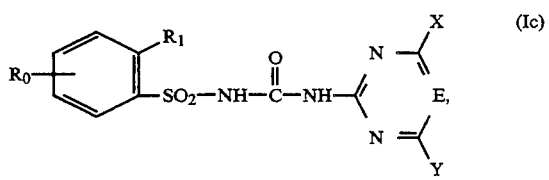

in which $R_0$, $R_1$, X, Y and E are as defined in claim 1.

5. A composition according to any one of claims 1 or 4, which comprises, as herbicide, a compound of the formula Id

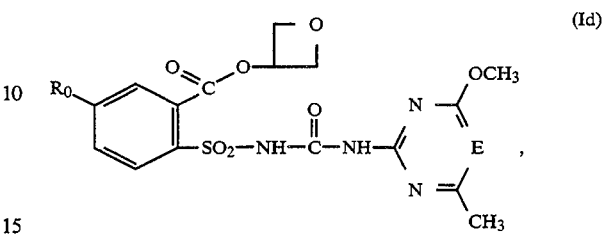

in which E is nitrogen or the methine group and $R_0$ is hydrogen or fluorine.

6. A composition according to claim 1, which comprises, as herbicide, a compound of the formula I in which Q is a radical

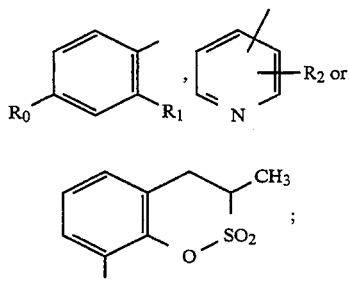

$R_0$ is hydrogen or halogen, in particular fluorine; $R_1$ is $C_1$-$C_3$monofluoroalkyl, difluoromethoxy, propargyloxy, ethynyl,

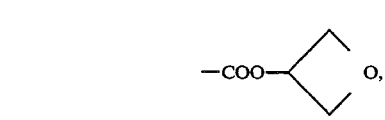

or a radical

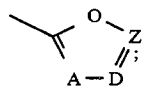

A and Z independently of one another are nitrogen or methine; D is nitrogen, methine or methylmethine; $R_2$ in the 2- or 3-position, alternating with the position of the —$SO_2NHCO$— group, is $C_1$- or $C_2$haloalkoxy, cyclopropylmethyleneoxy, $COOR_4$ or $NR_5R_6$; $R_4$ is methyl or 3-oxetanyl; $R_5$ is hydrogen, methyl or ethyl; $R_6$ is hydrogen, methyl, ethyl, —CHO, —$COCH_3$ or —$COC_2H_5$; X and Y independently of one another are methyl, methoxy, ethoxy or cyclopropyl; and E is nitrogen or the methine group.

7. A composition according to claims 1, which comprises, as safener, a 1,5-diphenylpyrazole-3-carboxylic acid derivative of the formula IIa

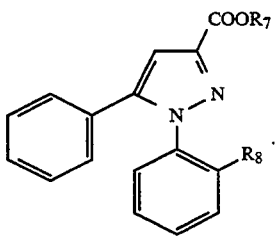

(IIa)

8. A composition according to claim 1, which comprises, as safener, a 1,5-diphenylpyrazole-3-carboxylic ester of the formula IIb

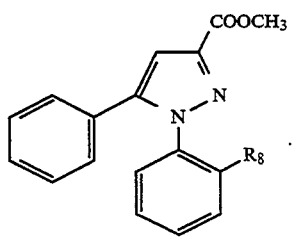

(IIb)

9. A composition according to claim 1, which comprises, as safener, a compound of the formula II in which $R_7$ is a hydrogen, $C_1$-$C_8$alkyl, methallyl, cyclohexyl, methylenyl, sodium, triethylammonium or isopropylammonium; $R_8$ is hydrogen or halogen; $R_9$ is hydrogen or chlorine; and $R_{10}$ is hydrogen, fluorine or chlorine.

10. A composition according to claim 1, which comprises, as safener, the compound of the formula IIc

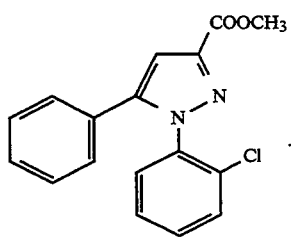

(IIc)

11. A composition according to claim 1, which comprises, as herbicide, N-[2-((3-oxetanyl)oxycarbonyl)-phenylsulfonyl]-N'-(4-methyl- 6-methoxypyrimidin-2-yl)urea and, as safener, a compound selected from amongst:

1-(2-chlorophenyl)-3-methoxycarbonyl-5-phenyl-pyrazole;

1-(2,4-dichlorophenyl)-3-methoxycarbonyl-5-phenyl-pyrazole;

1-(2-chlorophenyl)-3-benzyloxycarbonyl-5-phenyl-pyrazole;

1-(2-chlorophenyl)-3-methoxycarbonyl-5-(2,4-dichlorophenyl)pyrazole; or 1-(2-chlorophenyl)-3-methoxycarbonyl-5-(2-fluorophenyl)pyrazole.

12. A composition according to claim 1, which comprises, as safener, 1-(2-chlorophenyl)-3-methoxycarbonyl-5-phenylpyrazole and, as herbicide, a compound selected from amongst:

N-[2-(cyclopropylmethylenoxy)-3-pyridylsulfonyl]-N'-(4,6-dimethoxypyrimidin-2- yl)urea;

N-[3-(cyclopropylmethylenoxy)-2-pyridylsulfonyl]-N'-(4,6-dimethoxypyrimidin-2-yl)urea;

N-[3-dimethylamino-2-pyridylsulfonyl]-N'-(4,6-dimethoxypyrimidin-2-yl)urea;

N-[2-dimethylamino-3-pyridylsulfonyl]-N'-(4-methyl-6-methoxypyrimidin-2-yl)urea:

N-[3-dimethylamino-2-pyridylsulfonyl]-N'-(4-methyl-6-methoxypyrimidin-2-yl)urea;

N-[2((3-oxetanyl)oxycarbonyl)phenylsulfonyl]-N'-(4,6-dimethylpyrimidin-2-yl)urea;

N-[2-((3-oxetanyl)oxycarbonyl)phenylsulfonyl]-N'-(4-methyl-6-methoxypyrimidin-2-yl)urea;

N-[2-((3-oxetanyl)oxycarbonyl)phenylsulfonyl]-N'-(4,6-dimethoxypyrimidin-2-yl)urea;

N-[3-(difluoromethoxy-2-pyridylsulfonyl]-N'-(4-methyl-6-methoxypyrimidin-2-yl)urea;

N-[3-((3-oxetanyl)oxycarbonyl)-2-pyridylsulfonyl]-N'-(4,6-dimethoxypyrimidin-2-yl)urea; or N-[2-((3-oxetanyl)oxycarbonyl)-4-fluoro-phenylsulfonyl]-N'-(4-methyl-6-methoxypyrimidin-2-yl)urea.

13. A composition according to claim 1, comprising, as active ingredient, 2 to 95 % of a mixture of compounds of the formula II and of the formula I.

14. A method of protecting cereal crops against the harmful effect of the compounds of the formula I according to claim 1, which comprises treating the crops, the seed thereof or the area on which they are grown, simultaneously or independently of one another with an effective amount of a herbicide of the formula I according to claim 1 and a herbicide-antagonistically effective amount of a 1,5-diphenylpyrazole-3-carboxylic acid derivative of the formula II according to claim 1.

15. A method according to claim 14, wherein stands of crop plants or areas on which crop plants are grown are treated with 0.05 to 2 kg/ha of a compound of the formula I and an amount of 0.01 to 0.5 kg/ha of a compound of the formula II.

16. A method according to claim 14 for the selective control of weeds and grasses in cereal crops.

* * * * *